United States Patent [19]

Selwitz et al.

[11] 4,370,253

[45] * Jan. 25, 1983

[54] ALKENYLSUCCINIC ACID EMULSIONS AND THEIR PREPARATION

[75] Inventors: Charles M. Selwitz, Monroeville; Johann G. Schulz, Pittsburgh, both of Pa.

[73] Assignee: Gulf Research & Development Company, Pittsburgh, Pa.

[*] Notice: The portion of the term of this patent subsequent to Jan. 18, 2000, has been disclaimed.

[21] Appl. No.: 161,166

[22] Filed: Jun. 19, 1980

[51] Int. Cl.³ ............................................. B01J 13/00
[52] U.S. Cl. ................................ 252/312; 252/311.5; 562/595
[58] Field of Search ............................ 252/311.5, 312; 562/595, 590

[56] References Cited

U.S. PATENT DOCUMENTS 2,741,597  4/1956  Oosterhout et al. ............ 562/595 X
4,158,664  6/1979  Selwitz et al. ................ 562/595 X

*Primary Examiner*—Bernard Helfin
*Attorney, Agent, or Firm*—Deane E. Keith; Forrest D. Stine; Joseph J. Carducci

[57] ABSTRACT

A stable, isotropic emulsion of a water-insoluble material comprising alkenylsuccinic acid-in-water is prepared without an emulsifying agent. The emulsion is prepared by heating an admixture of a water-insoluble material comprising less than 95 weight percent alkenylsuccinic acid and water at a temperature of at least about 50° C., cooling the heated mixture to below about 30° C. and subjecting the cooled mixture to brisk agitation at a temperature below about 40° C. to form a stable emulsion. The remaining water-insoluble material can be an oleophilic material, such as high molecular weight olefins, paraffin wax, long chain alkyl aromatics, pine oil, or the like. The average particle diameter of the emulsion particles is less than about 30 microns.

20 Claims, No Drawings

ALKENYLSUCCINIC ACID EMULSIONS AND THEIR PREPARATION

CROSS-REFERENCE TO RELATED APPLICATION

Reference is made to the following U.S. application filed on even date, which application is hereby incorporated by reference.

U.S. patent application Ser. No. 161,113 to Charles M. Selwitz and J. G. Schulz entitled "Stable Emulsions of Substantially Pure Alkenylsuccinic Acid and Their Preparation."

FIELD OF THE INVENTION

The present invention relates to stable, aqueous emulsions of alkenylsuccinic acids and to the process for producing such stable emulsions. More particularly, this invention relates to stable, aqueous emulsions comprising alkenylsuccinic acids wherein such emulsions can be prepared without using emulsifying agents by a relatively simple procedure.

DESCRIPTION OF THE PRIOR ART

Alkenylsuccinic acids are useful in the production of cosmetics, for example, as components of hand lotions, in printing inks, and in floor polishes, for example, by incorporation into paraffin waxes to increase the hardness thereof. The use of the alkenylsuccinic acids in such products requires that it be emulsified in water for incorporation therein. However, conventional emulsifying agents, such as nitrogenous compounds including various amines, may cause skin irritations when the emulsion comes in contact with the skin.

U.S. Pat. No. 4,158,664 to C. M. Selwitz and H. I. Thayer discloses a process for improving the color of normally dark alkenylsuccinic anhydrides which involves treating such materials with water in order to produce a solid, light amber product having more commercial appeal. The use of the resulting product in an aqueous emulsion required the use of conventional emulsifying agents because of its waxy nature which renders it incompatable with water.

SUMMARY OF THE INVENTION

It has now been found that a stable, isotropic emulsion of alkenylsuccinic acids in water can be produced by a process which comprises heating an admixture of water and an alkenylsuccinic acid-containing normally water-insoluble material comprising less than about 95 weight percent alkenylsuccinic acid at the temperature above about 50° C., cooling the resulting mixture to a temperature below about 30° C., and then subjecting the admixture to brisk agitation while maintaining the temperature thereof below about 40° C., thereby forming a stable emulsion.

Surprisingly, it was found that despite the waxy nature of the alkenylsuccinic acid, it can be formed into a stable emulsion in the absence of conventional emulsifying agents, i.e., materials possessing both hydrophilic and lipophilic moieties, which aid in the formation of an emulsion. The normally water-insoluble material can comprise up to about 95 weight percent alkenylsuccinic acid, for example, between about 50 and about 93 weight percent, preferably between about 60 and about 75 weight percent. The remainder of the normally water-insoluble material can be, for example, oleophilic material which normally requires the use of an emulsifying agent to form a stable, aqueous emulsion. Thus, oleophilic organic materials including paraffin wax, high molecular weight olefins, long chain alkyl aromatics, pine oil and the like can be emulsified along with the alkenylsuccinic acid to form a stable emulsion. Thus, the alkenylsuccinic acid-in-water emulsions of the present invention experience no appreciable separation of water and the water-insoluble material within a period of at least 10 days.

DESCRIPTION OF THE PREFERRED EMBODIMENTS

The stable emulsions of the present invention are formed by heating an admixture of a water and normally water-insoluble material containing up to 95 weight percent alkenylsuccinic acid to a temperature of at least about 50° C., cooling the resulting mixture to a temperature below about 30° C. and then subjecting the admixture to brisk agitation while maintaining the temperature below about 40° C. to form a stable aqueous emulsion.

Any suitable alkenylsuccinic acid can be emulsified according to the present invention. One such alkenylsuccinic material has the following structural formula:

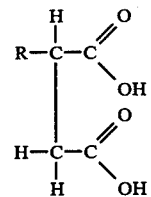

wherein R is an alkenyl group, straight or branched chain, having from 26 to 100 carbon atoms, preferably from 30 to 60 carbon atoms.

Suitable alkenylsuccinic acids and their corresponding anhydrides can be prepared in any conventional manner known in the art, including that described in U.S. Pat. No. 4,158,664 to Selwitz, et al, the disclosure of which is hereby incorporated by reference.

Thus, one procedure for preparing such compounds involves, for example, reacting, with stirring, a mixture of a straight or branched olefin and maleic anhydride at a molar ratio of olefin to maleic anhydride of about 0.5:1 to about 2:1, preferably about 0.8:1 to about 1.25:1 at a temperature of about 140° to about 250° C., preferably about 180° to about 220° C., and a pressure of about 0.1 to about 1000 pounds per square inch gauge (about 0.69 to about 6895 kPa), preferably about 10 to about 20 pounds per square inch gauge (about 68.95 to about 137.9 kPa), for about one to about 60 hours, preferably about six to about 24 hours. The olefin, or mixture of olefins, used will be straight or branched chain, but preferably straight, having from 26 to 100 carbon atoms, preferably from 30 to 60 carbon atoms. Such olefins can be obtained from any suitable source, but preferably are obtained by polymerizing ethylene in the presence of an aluminum alkyl catalyst, for example, as in U.S. Pat. No. 3,482,000 to Fernald, et al, or by cracking petroleum stocks, and paraffinic materials, such as microcrystalline wax and polyethylene. To separate any unreacted components that may be present the reaction mixture can be subjected to distillation at a temperature of about 150° to about 250° C., preferably about 180° C. to about 220° C., and a pressure of about 0.01 to about 10 pounds per square inch gauge (about 0.069 to about 68.95 kPa), preferably about 0.1 to about 0.5 pounds per square inch gauge (about 0.69 to about 3.45 kPa).

The resulting alkenylsuccinic anhydride can have the following structural formula:

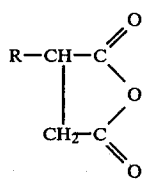

wherein R is an alkenyl group, straight or branched chain, but preferably straight, having from 26 to 100 carbon atoms, preferably from 30 to 60 carbon atoms.

When the alkenylsuccinic anhydride is admixed with water to form the emulsion, it is immediately converted to the corresponding acid.

The normally water-insoluble material to be emulsified can comprise up to about 95 weight percent alkenylsuccinic acid, for example, between about 50 and about 93 weight percent, preferably between about 60 and about 75 weight percent. The remainder of the water-in-soluble material can be, for example, the unreacted olefin remaining after the precursor alkenylsuccinic anhydride is prepared. Likewise, the remainder of the water-insoluble material can be materials utilized in the formation of floor polishes, hand lotions, printing inks, and the like, including oleophilic materials such as paraffin wax, high molecular weight olefins, long chain alkyl aromatics, pine oil and the like, which materials normally require the use of an emulsifier in order to form a stable, aqueous emulsion. The expression "normally water-insoluble material" as used herein refers to materials that are water-insoluble at ambient conditions.

As previously indicated, the mixture of water and normally water-insoluble material including alkenylsuccinic acid is heated to a temperature above about 50° C., generally in the range of between about 50° and about 150° C., preferably between about 50° and about 100° C. It is essential to the successful formation of a stable emulsion that the mixture of non-aqueous material comprising alkenylsuccinic acid, and water be heated to a temperature above about 50° C. Otherwise, the resulting emulsion will not be stable and the normally water-insoluble material will separate from the water.

The admixture of water and the normally water-insoluble material including alkenylsuccinic acid are heated to a temperature above about 50° C. and blended for at least about two minutes, preferably between about 10 and 120 minutes. The heating step may be conducted under any suitable pressure including ambient pressure conditions. However, elevated pressures can be utilized, for example, as high as 100 pounds per square inch gauge (689.5 kPa), or even higher, if elevated temperatures at utilized, in order to maintain the water in the system.

After the mixture is heated for the desired time the resulting mixture is cooled to a temperature below about 30° C., preferably to a temperature in the range of between about 10° and about 30° C. The cooled mixture is then vigorously stirred, while maintaining a temperature below about 40° C., preferably in the range of between about 10° and about 40° C., for at least about two minutes, preferably between about five and about 60 minutes.

The amount of water used relative to the normally water-insoluble material can vary over a wide range; however, a suitable range of water insoluble, alkenylsuccinic acid-containing material to water on a weight basis is between about 1/4 to about 10/1, preferably between about 1/1 and about 5/1.

Any suitable mixing device can be utilized including a colloid mill, a sonic mixer, or the like, which can reduce the particle size of the emulsion droplets to within the desired ranges. Thus, the degree of agitation should be sufficient to provide a stable emulsion. The term "stable emulsion" as used herein means that no appreciable separation of water and the emulsified water-insoluble material comprising alkenylsuccinic acid hereinafter occurs within a period of at least 10 days. The average particle diameter of the emulsion particles comprising the alkenylsuccinic acid of the present invention are, for example, between about two and about 30 microns, preferably between about three and about 10 microns, with an average particle diameter of between about four and about nine microns being especially preferred.

If desired, excess water can be removed from the emulsion by any suitable means, for example, by mechanical filtration. The resulting emulsion can contain alkenylsuccinic acid and water in a weight ratio of alkenylsuccinic acid to water in the range of between about 90/10 to about 20/80, preferably between about 50/50 and about 25/75.

The following examples illustrate the present invention and are not intended to limit the invention but, rather, are presented merely for purposes of illustration. In each of the examples, an alkenylsuccinic anhydride was used which was prepared by the following procedure. An alpha-olefin fraction was obtained from the product resulting from the telomerization of ethylene in the presence of triethyl aluminum at a temperature of about 200° C. and a pressure of about 3400 pounds per square inch gauge (about 24,443 kPa) over a period of 30–60 minutes and is further defined below in Table 1.

TABLE 1

| Isomer Distribution | Percent By Weight |
|---|---|
| Vinyl | 70.9 |
| Vinylidene | 20.6 |
| cis | 2.1 |
| trans | 4.3 |
| saturates | 2.0 |
| Iodine Number | 47.3 |
| Average Molecular Weight | 529 (corresponds to 37.8 carbon atoms per molecule) |
| Penetration, ASTM D156 | 12 (25° C.) |
|  | 28 (38° C.) |
| Color, Saybolt, ASTM D156 | +16 (white) |
| Melting Range, °C. | 55–75 |

A mixture of 397 grams of the specific alpha-olefin fraction defined above and 83.3 grams of maleic anhydride were stirred and heated at a temperature of about 193° to about 200° C. and ambient pressure in a nitrogen atmosphere for 16 hours. The pressure of the reaction mixture was then reduced to about five to 10 millimeters of mercury and distilled to recover the unreacted maleic anhydride, which amounted to 16.6 grams.

The remaining mixture constituted the alkenylsuccinic anhydride hereinafter used in the examples. The unreacted olefin present in the recovered alkenylsuccinic anhydride amounted to about 28 weight percent of the alpha olefin mixture used in preparing the alkenylsuccinic anhydride. When the alkenylsuccinic anhydride was used, it was converted to the corresponding alkenylsuccinic acid upon contact with water. Thus, the expression "alkenylsuccinic acid" as used herein includes the corresponding anhydride.

EXAMPLE I

One hundred forty-five milliliters of coal water (26° C.) and 50 grams of the above alkenylsuccinic acid mixture, which consists of 72 percent alkenylsuccinic acid and 28 percent olefin, were placed in a Waring blender and mixed for 13 minutes until the temperature reached 50° C. The temperature was above 40° C. for about three minutes. The mixture was cooled to room temperature (26° C.) and then blended in a Waring blender for five minutes, during which time the temperature of the mixture reached 29° C. The resulting stable emulsion, amounting to 195 grams, was found to contain 25.64 weight percent alkenylsuccinic acid and 74.35 weight percent water.

The following example illustrates the critical nature of the initial temperature to which the mixture must be heated.

EXAMPLE II

To a Waring blender there was added 145 grams of cold water and 50 grams of the above alkenylsuccinic acid mixture, which consists of 72 percent alkenylsuccinic acid and 28 percent olefin. The mixture was blended for about 12 minutes until a temperature of 39° C. was reached, after which it was cooled to room temperature. This procedure was repeated twice, with the highest temperature reached each time being 39° C. The resulting emulsion has a gritty texture and separated immediately into its component parts upon standing.

EXAMPLE III

To a Waring blender was added 145 grams of cold water and 69.4 grams of the above alkenylsuccinic acid mixture, which consists of 72 percent alkenylsuccinic acid and 28 percent olefin. The mixture was blended for 14 minutes until a temperature of 50° C. was reached. The mixture was at a temperature above 40° C. for about three minutes. The mixture was then cooled to room temperature and then blended again for about two minutes at a temperature of about 28° C. The resulting product was a smooth, stable emulsion.

Obviously, many modifications and variations of the invention, as hereinabove set forth, can be made without departing from the spirit and scope thereof.

We claim:

1. A process for preparing an aqueous emulsion, which comprises
   (a) heating a mixture of water and an alkenylsuccinic acid-containing normally water-insoluble material comprising oleophilic organic material and less than about 95 weight percent alkenylsuccinic acid having the formula

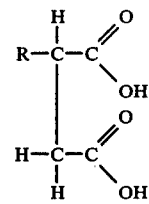

wherein R is an alkyl group having between about 26 and about 100 carbon atoms, at a temperature of between about 50° to about 150° C. for at least about 2 minutes,
   (b) cooling the resultant mixture to a temperature in the range of between about 10° and about 30° C.,
   (c) vigorously stirring the cooled mixture while maintaining the temperature in the range of between about 10° and below about 40° C. for at least about 2 minutes thereby forming a stable emulsion wherein the average particle diameter of the emulsion particles is between about 2 and about 30 microns.

2. The process of claim 1 wherein said process is conducted in the absence of an emulsifying agent.

3. The process of claim 1 wherein said heating is conducted at a temperature in the range of between about 50° and about 150° C. for a period of between about 10 and about 120 minutes.

4. The process of claim 1 wherein said emulsion comprises particles of said water-insoluble material having an average particle diameter of between about three and about 10 microns.

5. The process of claim 1 wherein said emulsion is filtered to remove excess water.

6. The process of claim 1 wherein said water-insoluble material comprises between about 50 and about 93 weight percent alkenylsuccinic acid.

7. The process of claim 1 wherein said water-insoluble material comprises high molecular weight olefinic material.

8. The process of claim 1 wherein said water-insoluble material comprises paraffin wax.

9. The process of claim 1 wherein said water-insoluble material comprises pine oil.

10. The process of claim 1 wherein said mixture is heated to a temperature in the range of between about 50° and about 100° C.

11. The process of claim 1 wherein said mixture is heated for a period of between about 10 and about 120 minutes.

12. The process of claim 1 wherein said emulsion particle size is between about 3 and about 10 microns.

13. An alkenylsuccinic acid-in-water emulsion prepared in accordance with claim 1, wherein said water-insoluble material comprises up to 95 weight percent alkenylsuccinic acid.

14. A stable emulsion comprising emulsion particles of an alkenylsuccinic acid-containing normally water-insoluble material comprising oleophilic organic material and up to 95 weight percent alkenylsuccinic acid in water, wherein said alkenylsuccinic acid has the formula

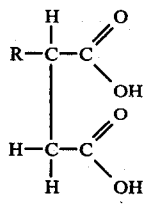

wherein R is an alkyl group having between about 26 and about 100 carbon atoms, said emulsion particles having an average particle diameter of between about 2 and about 30 microns.

15. The emulsion of claim 14 wherein said emulsion contains no emulsifying agent for said alkenylsuccinic acid.

16. The emulsion of claim 14 wherein said emulsion particles have an average particle diameter of between about 3 and about 10 microns.

17. The emulsion of claim 14 wherein said water-insoluble material comprises between about 50 and about 93 weight percent alkenylsuccinic acid.

18. The emulsion of claim 17 wherein said water-insoluble material comprises high molecular weight olefinic material.

19. The emulsion of claim 17 wherein said water-insoluble material comprises paraffin wax.

20. The emulsion of claim 17 wherein said water-insoluble material comprises pine oil.

* * * * *